United States Patent [19]

Ikezawa et al.

[11] Patent Number: 5,480,660
[45] Date of Patent: Jan. 2, 1996

[54] HYPOALLERGENIC WHEAT PREPARATION, PROCESS FOR PRODUCING THE SAME, AND PROCESSED FOOD INCLUDING THE SAME

[75] Inventors: Zenro Ikezawa, Yokohama; Shumpei Yokota, Chigasaki; Kazufumi Tsubaki, Tokyo; Hiroshige Kohno, Tokyo; Hiromu Sugiyama, Tokyo; Kenji Ikeda, Tokyo; Takashi Suzuki, Tokyo, all of Japan

[73] Assignee: Asahi Denka Kogyo K.K., Tokyo, Japan

[21] Appl. No.: 273,273

[22] Filed: Jul. 11, 1994

Related U.S. Application Data

[60] Continuation of Ser. No. 914,998, Jul. 16, 1992, abandoned, which is a division of Ser. No. 685,516, Apr. 15, 1991, abandoned.

[30] Foreign Application Priority Data

Apr. 16, 1990 [JP] Japan ................. 2-99562

[51] Int. Cl.$^6$ .................................... A23J 3/00
[52] U.S. Cl. .............. 426/2; 426/804; 426/622; 426/549
[58] Field of Search .................. 426/2, 622, 618, 426/656, 549, 804

[56] References Cited

U.S. PATENT DOCUMENTS

| | | | |
|---|---|---|---|
| 2,504,962 | 4/1950 | Burdick | 530/375 |
| 2,797,212 | 6/1957 | Miley et al. | 530/375 |
| 2,801,236 | 7/1957 | Miley | 530/375 |
| 2,961,353 | 11/1960 | Carlson et al. | 530/375 |
| 3,574,180 | 4/1971 | Johnston | 530/375 |
| 3,661,593 | 5/1972 | Christianson et al. | |
| 3,790,553 | 2/1974 | Rao et al. | 530/375 |
| 4,208,323 | 6/1980 | Murray et al. | 530/375 |
| 4,285,862 | 8/1981 | Murray et al. | 530/375 |
| 4,508,736 | 4/1985 | Bean et al. | 426/622 |

FOREIGN PATENT DOCUMENTS 2126867 4/1984 United Kingdom.

OTHER PUBLICATIONS

Febs Letters, vol. 261, No. 1, Feb. 1990, Amsterdam NL pp. 85–88; Gomez L. et. al. "Members of the alpha–amylase inhibitors family from wheat endosperm are major allergens associated with baker's asthma".

Clinical Allergy, vol., 15, No. 2, 1985, London, pp. 203–210; Prichard, M. G. et al.: "Skin test and RAST responses to wheat and common allergens and respiratory disease in bakers."

A. E. Bender, Dietetic Foods, 1968, pp. 34–39, Chemical Publishing, New York.

E. J. Pyler, Baking Science & Technology, Published by Siebel Publishing Co., 1973, Chicago, Ill., pp. 104–118.

Roy L. Whistler, James N. Bemiller, Eugene F. Paschall; Starch: Chemistry and Technology; Academic Press, Inc. 1984, pp. 491–505.

*Primary Examiner*—Carolyn Paden
*Attorney, Agent, or Firm*—Burgess, Ryan & Wayne

[57] ABSTRACT

A wheat preparation with a reduced content of proteins of molecular weights of not more than 30,000. A process for producing the same, and a processed food including the same are also disclosed. The processed food is effective for patients with allergy to wheat.

3 Claims, 1 Drawing Sheet

HYPOALLERGENIC WHEAT PREPARATION, PROCESS FOR PRODUCING THE SAME, AND PROCESSED FOOD INCLUDING THE SAME

This application is a continuation of application Ser. No. 07/914,998, filed Jul. 16, 1992, now abandoned, which is a division of application Ser. No. 07/685,516, filed Apr. 15, 1991, now abandoned.

BACKGROUND OF THE INVENTION

1. Field of the Invention

The present invention relates to a hypoallergenic wheat preparation, a process for the production of the same, and a food product containing the same.

2. Description of the Related Art

Allergies are adverse immune reactions and are caused by the entry of foreign substances (allergens) into the body.

In recent years, the number of patients with allergy has soared. This is due to the ingestion of large amounts of protein along with the westernization of the diet. Further, other factors (for example, atmospheric pollution caused by exhaust gas and installation of carpets in western style homes with their high air-tightness and other facets of westernization of lifestyles) are complicatedly superimposed and various types of substances existing in the living environment are changed into allergens.

Food allergies to wheat and other cereals have also been soaring. Such food allergies often appear in infants and the adults and cause physical and mental distress to the sufferers, of course, and also great mental distress to their parents and families as a whole.

As a method for treatment of patients with food allergy, attempts have been made to limit or ban the ingestion of food which would be the cause of such problems. However, limitation of foods could inhibit the maintenance of life and growth. Therefore, a desirable method would be to have them ingest food from which the allergy causing components had been removed but where other nutritional components had not been impaired.

In the past, however, the specific antigen substance (allergen) in wheat and other cereals causing allergies in patients had not been clarified and had not been specified. Therefore, it has not been clear which component should be selectively removed or reduced and what method should be used for this purpose. It has only been reported, with respect to rice allergies, that the fraction of rice protein soluble in saline water is high in antigenicity (Miyakawa et al, 1988 Allergy Gakkai Yoshishu). Allergies, however, are immune reactions with extremely high specificity and it would be difficult to apply the discovery with regard to rice allergies to wheat allergies.

The present inventors analyzed in detail the components of wheat so as to solve the above problems and therefore investigated and examined the sera of persons suffering from allergies to wheat and the sera of normal persons. As a result, they discovered that it is possible to alleviate the onset of the allergies in patients with allergies to wheat by eliminating or reducing, from flour, proteins having molecular weights of not more than 30,000 or proteins having molecular weights of not more than 30,000 and proteins having molecular weights of 50,000 to 70,000. The present invention is based on this discovery.

SUMMARY OF THE INVENTION

Accordingly, the object of the present invention is to provide a hypoallergenic wheat preparation effective as food for patients with allergies to wheat, a process for production of the same (that is, a process reducing the allergenicity of wheat preparations), and processed food products from the hypoallergenic wheat preparation.

Other objects and advantages of the present invention will be apparent from the following description.

In accordance with the present invention, there is provided a wheat preparation with a reduced content of proteins of molecular weights of not more than 30,000 (hereinafter optionally referred to as a "hypoallergenic wheat preparation").

Further, in accordance with the present invention, there is provided a process for producing a wheat preparation with a reduced content of proteins of molecular weights of not more than 30,000 (that is, a hypoallergenic wheat preparation), characterized in that a wheat preparation is treated by water or a saline solution to remove the soluble components.

Still further, in accordance with the present invention, there is provided a processed food containing a wheat preparation obtained using a wheat preparation with a reduced content of proteins of molecular weights of not more than 30,000 (that is, a hypoallergenic wheat preparation).

DESCRIPTION OF THE PREFERRED EMBODIMENTS

Figure 1:
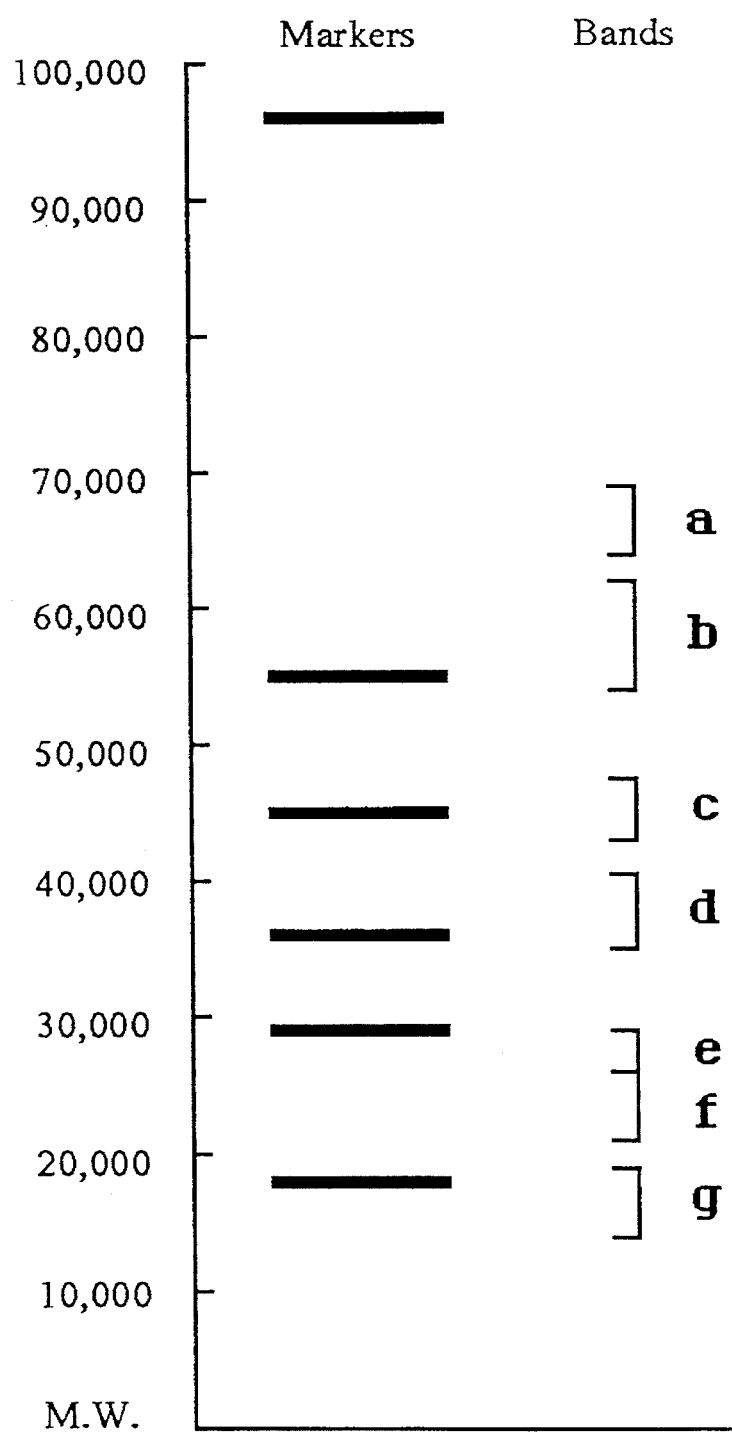
FIG. 1 is an explanatory view showing the state of separation of the protein bands obtained by electrophoresis of a wheat extract.

In this specification, the term "wheat preparation" means the material produced by removing the husk from the seeds of wheat (that is, kernels) and conditioning and processing the raw kernels (for example, milling, swelling, or agglutination). Therefore, powder, grains, or paste are included, with powder preferable.

The preferable wheat preparation is flour. As the flour, use may be made of "high strength" flour, "medium strength" flour, and "low strength" flour (referring to Japanese grades), or flour gluten, but in view of the processing and ease of acquisition, commercially prepared flour is preferable.

In the hypoallergenic wheat preparation of the present invention, the content of the protein fractions with molecular weights of not more than 30,000 (in particular, the fractions with molecular weights of 14,000 to 19,000, 21,000 to 26,000, and 26,000 to 29,000) is reduced compared with unprocessed wheat preparations. Further, in the hypoallergenic wheat preparation of the present invention, in addition to reducing the said content of protein fractions with molecular weights of not more than 30,000, it is desirable to reduce the content of the protein fractions with molecular weights of 50,000 to 70,000. By reducing the content of the protein fractions with molecular weights of 50,000 to 70,000, it is possible to provide a preparation which can be ingested by more diverse allergy sufferers to wheat.

The hypoallergenic wheat preparation of the present invention, when 1M-NaCl (10 ml) is added to 1 g of the preparation and the whole is stirred for 30 minutes at room temperature, has a concentration of proteins with molecular weights of not more than 30,000, included in the supernatant, of not more than 500 µg/ml, preferably not more than 200 μg/ml, more preferably not more than 100 μg/ml. Further, the concentration of proteins of molecular weights of-50,00 to 70,000 included in the supernatant is not more than 100 μg/ml, preferably not more than 80 μg/ml, more preferably not more than 60 μg/ml.

The hypoallergenic wheat preparation of the present invention may be produced by treating a wheat preparation (for example, flour) with water or a saline solution so as to remove its soluble component.

As the salt, use may be made of salts of inorganic acids (for example, hydrochloric acid, sulfuric acid, or phosphoric acid) and alkali metals (for example, sodium and potassium), in particular, sodium chloride, potassium chloride, sodium sulfate, sodium carbohydrate, sodium polyphosphate, and various phosphoric acid salts are preferable.

The concentration of the saline solution is not more than 5M, preferably in particular not more than 3M. If use is made of a saline solution with a concentration higher than 5M, then the dissolution of the protein acting as the allergen would not be sufficient and further the processing for removal of the salt would become complicated.

Specifically, water (for example, one to 20 times the amount of the flour) is added to the wheat powder, the mixture is stirred for 10 minutes to 72 hours, preferably 1 to 10 hours, then allowed to stand or centifugally separated, then for example a 0.05M to 5M concentration of an aqueous solution of sodium chloride is added in an amount of 2 to 20 times the amount, preferably 3 to 10 (more preferably 5 to 10) times the amount, and stirred for 10 minutes to 72 hours, preferably 1 to 10 hours, whereby the fraction of proteins of molecular weights of not more than 30,000 and the fraction of proteins of molecular weights of 50,000 to 70,000 are dissolved out, then the resulting product is allowed to stand or is centrifugally separated to obtain a precipitate, the hypoallergenic wheat preparation of the present invention. This operation is repeated several times, if necessary. Usually, once to five times (preferably 3 to 5 times) is sufficient. Further, this operation may be performed batchwise or continuously.

After the dissolution processing by the saline solution, the preparation may be rinsed to remove the salt and further additionally drive out the water soluble allergens. This operation can be repeated, if necessary. Usually, it is recommended to perform three to five times. Further, to promote the dissolution out of the protein to be removed, use may be made at the same time of a protease, for example, papain, trypsin, pepsin, pancreatin, actinase, or alpha-chemotrypsin.

Whether or not the fraction of proteins of molecular weights of not more than 30,000 and the fraction of proteins of molecular weights of 50,000 to 70,000 are fully dissolved out and the hypoallergenic wheat preparation of the present invention is obtained may be judged by checking the existence of protein fractions to be removed by the method of electrophoresis or high performance liquid chromatography. For further strict measurement, use may be made of an immunochemical analysis method, for example, the enzyme immunoassay method or the radio immunoassay method.

The hypoallergenic wheat preparation of the present invention obtained in this way may, depending on the application, be used without subsequent treatments, or dried and used as a powder or grains.

The drying method may be any method used for drying food. For example, it is possible to use spraying, vacuum, hot air, freezing, natural sunlight, electromagnetic waves, or combinations of the same. As the powder making means, use may be made of the roll system, motar system, impact system, or other methods.

The hypoallergenic wheat preparation of the present invention may, just like the conventional wheat preparation, be used as a material for processed food. As the processed food, for example, mention may be made of bakery products or baked confectionery products (for example, bread, biscuits, crackers, and cookies), western style fresh confectionery (for example, cookies), noodle products (for example, Japanese udon noodles, Chinese noodles, pasta, and Japanese soba noodles), cooking products, etc. In particular, it is effective in improving the palatability of noodle products.

As explained above, the hypoallergenic wheat preparation of the present invention can be easily manufactured by simple processing from commercially available flour etc., so processed food with reduced allergens can be cheaply supplied. Further, even the palatability can be improved by preparing noodles from the hypoallergenic wheat preparation of the present invention.

EXAMPLES

The present invention now will be further illustrated by, but is by no means limited to, the following Examples.

A. Examples of Test of Action for Preventing Allergies

Example A-1

To 1 g of flour (made by Nippon Seifun Co.; high strength flour) was added 10 ml of 76 mM tris-citrate buffer solution (pH 7.4) including 1M-NaCl, which mixture was stirred for 14 hours at 4° C. Next, the mixture was centrifugally separated for 20 minutes (10,000×G) and the supernatant (extract) was separated. This extract was dialyzed at 4° C. for 24 hours using 0.15 mM-NaCl containing 20 mM phosphoric acid buffer (pH 7.4) by a dialysis tube (pore size molecular weight 3500 cut). The dialyzed extract was freeze dried to obtain a salt extract. This extract was used as the extract A.

On the other hand, 20 ml of 76 mM tris-citrate buffer solution (pH 7.4) including 1M-NaCl was added to the wheat residue obtained as a precipitate in the centrifugal processing, and the mixture was stirred for 14 hours at 5° C., and then further rinsed for 2 hours. The concentration of protein in the supernatant (10 ml) obtained by this rinsing was 14 μg/ml.

The rinsed wheat residue was freeze dried, 10 ml of a urea extraction agent (76 mM tris-citrate buffer solution including 7M urea and 20 mM 2-mercaptoethanol) was added to 0.8 g of the dried product, then the mixture was stirred for 10 minutes at room temperature. Next, the mixture was centrifugally separated for 20 minutes (10,000×G) and the supernatant (urea extract) was separated. The extract was dialyzed in the same way as the above. The dialyzed extract was freeze dried to obtain the salt extract. This extract was used as the extract B.

The extract A and the extract B were redissolved in 10 ml of the extraction agent solution for each extract, respectively, and filtered by 0.22 μm millipore filters.

Next, the extract A and the extract B corresponding to 2 mg of protein mass were taken. The reagents were added thereto to give a final concentration of 1 percent of SDS, 1 percent of 2-mercaptoethanol, 1 mM of tris-hydrochloride buffer solution, and 20 percent of glycerine. The whole was diluted to 1 ml by distilled water and the samples for electrophoresis (SDS-PAGE) were prepared.

These samples were heat treated at 100° C. for 2 minutes, then BPB (bromophenol blue) was added to 0.05 percent. 5 μl of the samples were added to 10 to 20 percent gradient SDS-polyacrylamide gel, subjected to electrophoresis at 40 mA for 70 minutes, and the sample A (salt extract of wheat) and the sample B (urea extract of wheat) were fractionated.

At that time, the electrophoresis was performed while simultaneously passing to the plate proteins (molecular weights of 96,000, 55,000, 45,000, 36,000, 29,000, and 18,000) with known molecular weights as markers. The results were shown in FIG. 1 and bands were obtained at the regions a to g.

Next, the wheat protein fractions indicated by the band a to band g were transferred electrophoretically to a Millipore Co. Imobilon P film with a fixed current of 80 mA for one hour. The transferred film was blocked with 5 percent skimmed milk, then the sera of patients with wheat allergy (total 7) and the sera of adults with no wheat allergy (control) were reacted for 14 hours at room temperature.

The film was rinsed, then a 500 dilution of biotin bonded antihuman IgE (made by Tago Co.) and peroxidase bonded avidin (×1000 dilution) were reacted for 2 hours each at 37° C., then the IgE antibody bonded to the film was labelled by the enzyme.

On the other hand, 25 ml of DAB (3,3-diaminobendizene tetrahydrochloride) was dissolved in 100 ml of 50 mM tris-hydrochloride buffer solution (pH 7.6), 50 μl of hydrogen peroxide (30%) was added, and a color forming solution was prepared.

The color forming solution was added to the abovementioned transfer film and IgE antibodies were detected. The results are shown in Table 1 and Table 2. In Table 1 and Table 2, sera No. 1 to No. 7 were sera of patients with allergy to wheat, while sera No. 8 to No. 10 were sera of healthy persons (control). Further, the evaluations shown in Table 1 (salt extract) and Table 2 (urea extract) were made as follows according to the bands obtained by electrophoresis:

−: No bands detected

+: Bands observed

++: Bands observed considerably strongly

+++: Bands observed extremely strongly

As clear from. Table 1 and Table 2, the sera of patients were strongly reacted to the salt extract, in particular, strongly reacted to the protein components fractionated at molecular weights of not more than 30,000. Further, there was a slight reaction to the protein components fractionated at molecular weights of 50,000 to 70,000. As opposed to this, the sera of patients were not reacted much at all to the extract B and no difference was observed with the sera of healthy persons. The fraction component to which the sera of patients displayed specificity was not observed in the extract B.

TABLE 1

| Serum No. | Band a | Band b | Band c | Band d |
|---|---|---|---|---|
| 1 | + | − | + | ++ |
| 2 | − | − | + | ++ |
| 3 | − | − | + | ++ |
| 4 | + | − | + | ++ |
| 5 | − | − | + | ++ |
| 6 | − | − | + | ++ |
| 7 | − | + | + | ++ |
| 8 | − | − | + | ++ |
| 9 | − | − | + | ++ |
| 10 | − | − | + | ++ |

| Serum No. | Band e | Band f | Band g |
|---|---|---|---|
| 1 | ++ | ++ | +++ |
| 2 | ++ | ++ | +++ |
| 3 | ++ | − | +++ |
| 4 | ++ | ++ | +++ |
| 5 | ++ | ++ | +++ |
| 6 | ++ | − | +++ |
| 7 | ++ | − | +++ |
| 8 | − | − | − |
| 9 | − | − | − |
| 10 | − | − | − |

TABLE 2

| Serum No. | Band a | Band b | Band c | Band d |
|---|---|---|---|---|
| 1 | + | − | + | + |
| 2 | + | − | + | + |
| 3 | + | − | + | + |
| 4 | + | − | + | + |
| 5 | + | − | + | + |
| 6 | + | − | + | + |
| 7 | + | − | + | + |
| 8 | + | − | + | + |
| 9 | + | − | + | + |
| 10 | + | − | + | + |

| Serum No. | Band e | Band f | Band g |
|---|---|---|---|
| 1 | − | − | − |
| 2 | − | − | − |
| 3 | − | − | − |
| 4 | − | − | − |
| 5 | − | − | − |
| 6 | − | − | − |
| 7 | − | − | − |
| 8 | − | − | − |
| 9 | − | − | − |
| 10 | − | − | − |

Example A-2

To 1 g of flour (made by Nippon Seifun; product name Eagle) was added 10 ml of urea extract used in Example A-1. The extraction of the wheat protein and purification were performed by the same method as in Example A-1 to obtain the urea extract. This was used as the extract C.

The extract C and the extract B of Example A-1 were added in 10 g amounts to 50 percent glycerine solutions of 1M-NaCl and the resulting mixtures were stirred for 14 hours at 4° C. Next, centrifugal separation (10,000×G) was performed for 20 minutes to obtain the supernatants. These extracts were used as the extract sample B and the extract sample C.

Patients with allergy to wheat (total 5) were made to lie face down, one arm was disinfected by an alcohol swab, the arm was allowed to naturally dry, then the extract sample B, extract sample C, and control solution (50% glycerine 1M-NaCl solution) were dropped, one drop each, on the arm as antigen solutions. A sterilized needle was pierced into the skin in a slanted direction through the dropped antigen solutions and judgement was made as the existence of blisters and surrounding rashes after 20 minutes. The judgement was made as follows in accordance with the method of Sheldon J. M. et al. (A manual of clinical allergy 159, W. B. Saunders Company, Philadelphia and London, 1967):

−: Case same as control sample (negative)

±: Case where judgement of rash is difficult

+: Case where rash is observed, but diameter is not more than 21 mm

++: Case where rash of over 21 mm is observed, but there are no blisters

+++: Case where rashes and blisters are both observed.

The results are shown in Table 3. As clear from Table 3, in extract B, no allergenic activity was observed, while it was observed in extract C. That is, it was manifest that flour treated with water and a saline solution has no allergenic activity.

TABLE 3

| Patient No. | Extracted sample B | Extracted sample C | Control |
| --- | --- | --- | --- |
| 1 | ± | +++ | − |
| 2 | − | ++ | − |
| 3 | − | +++ | − |
| 4 | ± | +++ | − |
| 5 | − | ++ | − |

B. Examples of Manufacture

Example B-1

2 kg of commercial flour (made by Nippon Seifun: high strength flour) was placed in a container (10 liters), 5 kg of water was added, and the mixture was stirred for 2 hours at 5° C. Further, centrifugal separation was performed (8000 rpm) to obtain the precipitate. This precipitate was subjected to the same extraction processing two times repeatedly. 1M-NaCl solution (7 kg) was added to the resultant precipitate, and the same stirring and centrifugal separation were performed as the above, and the supernatant was removed. The processing by NaCl was repeated one more time. Further, 8 liters of water were added to the resultant precipitate, and the whole was stirred for 2 hours and the supernatant was removed. The resultant precipitate was spray dried with hot air to obtain 1.8 kg of a flour preparation. This flour preparation was negative when investigated as to the intracutaneous reaction of wheat allergy sufferers.

Further, when the protein fraction of the resultant flour preparation was measured by the electrophoresis method, it was found that the amount of protein fractions with molecular weights of not more than 30,000 was 500 μg/10 g of flour and the amount of protein fractions with molecular weights of 50,000 to 70,000 was 20 μg/1 g of flour.

Example B-2

The processing described in Example B-1 was repeated to prepare a wheat preparation, but as the flour, low strength flour (made by Nippon Seifun) was used, instead of high strength flour. The resultant wheat preparation was negative when investigated as to intracutaneous reaction of patients with allergy to wheat. Further, the protein fraction of the resultant wheat preparation was measured by the same method as in Example B-1, whereupon it was found that the amount of protein fractions with molecular weights of not more than 30,000 was 30 μg/10 g of flour and the amount of protein fractions with molecular weights of 50,000 to 70,000 was 50 μg/1 g of flour.

Example B-3

500 g of the flour preparation obtained in Example B-1, 500 g of the flour preparation obtained in Example B-2, 18 g of sodium chloride, and 100 g of water were blended with a lateral mixer, the mixture was made into a sheet, and the sheet was extruded by an extruder to make noodles (Japanese Udon). The resultant noodles were fed to seven patients with allergy to wheat in an amount of 20 g a day for three days, whereupon no onset was observed due to the ingestion.

Although the present invention has been described with reference to specific embodiments, various changes and modifications obvious to those skilled in the art are deemed to be within the spirit, scope and concept of the invention.

We claim:

1. A method for preventing the onset of allergies of a person afflicted with allergies to wheat, comprising administering to said person, a processed food containing a wheat preparation with a reduced content of proteins of molecular weights of 14,000 to 19,000, 21,000 to 26,000, 26,000 to 29,000 and 50,000 to 70,000, said wheat preparation with the reduced content being produced by affecting an ordered sequence of treatment to wheat flour with water, then a saline solution and further water to remove soluble components, and wherein said treatment resulted in a concentration of said proteins of molecular weights of 14,000 to 19,000, 21,000 to 26,000 and 26,000 to 29,000, being not more than 5000 μg/ml, as determined in a supernatant obtained by adding 10 ml of 1M-NaCl to 1 g of said wheat preparation with the reduced content and stirring for 30 minutes at room temperature, and a concentration of said proteins of molecular weights of 50,000 to 70,000, included in said supernatant, being not more than 100 μg/ml.

2. A method according to claim 1, wherein said ordered sequence of treatment comprises:

adding water in an amount of 1 to 20 times the amount of the flour, stirring the mixture for 10 minutes to 72 hours, centrifugally separating insoluble components, adding the saline solution in an amount of 2 to 20 times the amount of the insoluble components, stirring the resulting mixture for 10 minutes to 72 hours, centrifugally separating the insoluble components and rinsing the insoluble components with water.

3. A method according to claim 1, wherein the allergy is allergic dermatitis.

* * * * *